United States Patent
Cook et al.

(10) Patent No.: US 10,874,518 B2
(45) Date of Patent: Dec. 29, 2020

(54) MAGNETIC PROSTHETIC IMPLANTS AND METHODS THEREOF

(71) Applicant: Fellowship of Orthopaedic Researchers, Inc., Metairie, LA (US)

(72) Inventors: Stephen D. Cook, Metairie, LA (US); Laura P. Patron, Belle Chase, LA (US); Michael C. Harrison, Metairie, LA (US); Liam P. Nolan, New Orleans, LA (US)

(73) Assignee: Fellowship of Orthopaedic Researchers, Inc., Metairie, LA (US)

(*) Notice: Subject to any disclaimer, the term of this patent is extended or adjusted under 35 U.S.C. 154(b) by 287 days.

(21) Appl. No.: 15/707,937

(22) Filed: Sep. 18, 2017

(65) Prior Publication Data

US 2019/0083266 A1    Mar. 21, 2019

(51) Int. Cl.
*A61F 2/28*    (2006.01)
*A61F 2/30*    (2006.01)
(Continued)

(52) U.S. Cl.
CPC .......... *A61F 2/2814* (2013.01); *A61F 2/601* (2013.01); *A61F 2/68* (2013.01); *A61F 2/78* (2013.01);
(Continued)

(58) Field of Classification Search
CPC .............. A61F 2/2814; A61F 2002/607; A61F 2002/30079
See application file for complete search history.

(56) References Cited

U.S. PATENT DOCUMENTS

| 4,024,588 A | * | 5/1977 | Janssen | ..................... A61F 2/30 |
| | | | | 623/18.12 |
| 5,507,835 A | * | 4/1996 | Jore | ......................... A61F 2/38 |
| | | | | 623/33 |

(Continued)

FOREIGN PATENT DOCUMENTS

| DE | 102011113918 A1 | 3/2013 |
| EP | 1743602 A1 | 1/2007 |
| WO | WO-2010070614 A1 * | 6/2010 | ............... A61F 2/78 |

OTHER PUBLICATIONS

International Search Report and Written Opinion by the International Searching Authority in PCT Application No. PCT/US2018/051589, dated Jan. 16, 2019.

(Continued)

*Primary Examiner* — Bruce E Snow
*Assistant Examiner* — Melissa A Hoban
(74) *Attorney, Agent, or Firm* — Grimes & Yvon LLP

(57) ABSTRACT

Prosthetic implant devices and related methods are provided. The prosthetic implant devices include an internal component and an external component. The internal component has an implant portion associated with one or more rare earth magnets. The internal component being of a size and shape suitable for surgical implantation into the residual limb of the amputee. The one or more rare earth magnets generate at least one magnetic field. The external component having a prosthetic piston associated with a plurality of magnetic elements and a prosthetic cup associated with a magnetic array. The magnet elements of the prosthetic piston being in adaptable magnetic association with the at least one magnetic field generated by the one or more rare earth magnets.

17 Claims, 13 Drawing Sheets

(51) Int. Cl.
*A61F 2/68* (2006.01)
*A61F 2/78* (2006.01)
*A61F 2/60* (2006.01)
A61F 2/74 (2006.01)
A61F 2/80 (2006.01)
A61F 2/54 (2006.01)
A61F 2/50 (2006.01)

(52) U.S. Cl.
CPC . *A61F 2/54* (2013.01); *A61F 2/60* (2013.01); *A61F 2/80* (2013.01); *A61F 2002/30079* (2013.01); *A61F 2002/5006* (2013.01); *A61F 2002/5084* (2013.01); *A61F 2002/6863* (2013.01); *A61F 2002/74* (2013.01); *A61F 2002/7887* (2013.01)

(56) References Cited

U.S. PATENT DOCUMENTS

| | | | |
|---|---|---|---|
| 7,922,773 B1 | 4/2011 | Kuiken | |
| 9,351,854 B2* | 5/2016 | Jonsson | A61F 2/66 |
| 2004/0138663 A1* | 7/2004 | Kosashvili | A61B 17/7216 |
| | | | 606/62 |
| 2005/0261783 A1 | 11/2005 | Geilman et al. | |
| 2006/0293762 A1 | 12/2006 | Schulman et al. | |
| 2009/0112207 A1 | 4/2009 | Walker et al. | |
| 2009/0112262 A1 | 4/2009 | Pool et al. | |
| 2009/0112263 A1 | 4/2009 | Pool et al. | |
| 2009/0254196 A1* | 10/2009 | Cox | A61F 2/2814 |
| | | | 623/33 |
| 2011/0224805 A1 | 9/2011 | Schulman et al. | |
| 2012/0157996 A1 | 6/2012 | Walker et al. | |
| 2013/0006356 A1* | 1/2013 | Cook | A61F 2/78 |
| | | | 623/16.11 |
| 2016/0236771 A1 | 8/2016 | Necci | |

OTHER PUBLICATIONS

International Search Report and Written Opinion by the International Searching Authority in PCT Application No. PCT/US2012/045316, dated Oct. 11, 2012.

\* cited by examiner

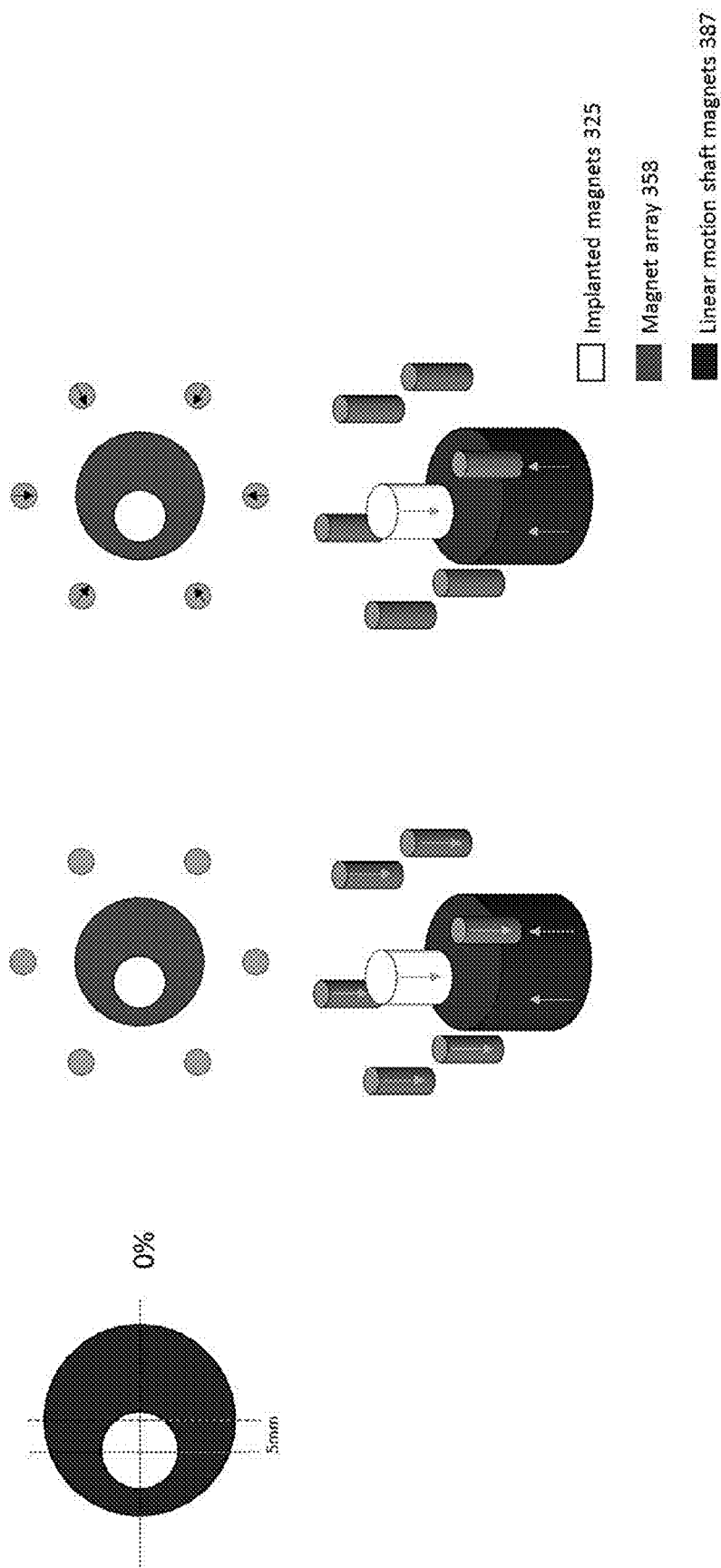

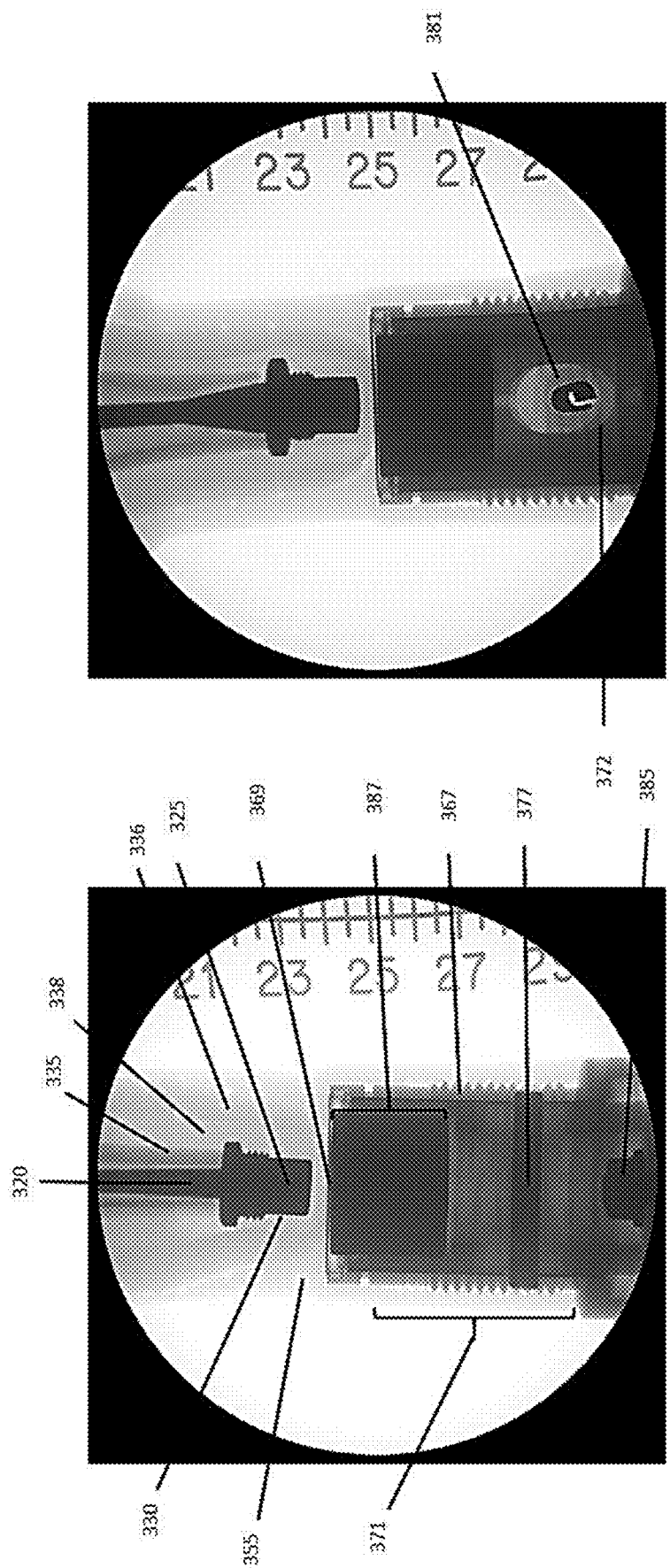

MAGNETIC PROSTHETIC IMPLANTS AND METHODS THEREOF

FIELD OF THE INVENTION

This disclosure relates generally to prosthetic devices. In particular, this disclosure relates to prosthetic devices having internal magnetic forces and methods thereof.

BACKGROUND OF THE INVENTION

Prosthetic devices for upper or lower limbs are generally designed based on appearance and/or functional needs. Several designs for such devices are known in the art, two examples of which are illustrated in FIGS. 1 and 2.

FIG. 1 shows prior art prosthetic device 100, which includes a prosthetic 105 affixed, via a socket connector 110, to a prosthetic socket 115. The prosthetic socket 115 may have been a "sleeve" or "jacket" into which the residual limb 120 (having a bone 125) may have been affixed through suitable connections such as compressive vacuum, suction, straps, elastic band, and the like (not shown). Optionally, a gel liner 130 may have been used to aid in comfort and/or fit.

FIG. 2 shows an alternative prior art prosthetic device 200, which includes a female implant 205 surgically implanted into a bone 210 of a residual limb 215. A connecting screw 220 is screwed into the female implant 205 through an abutment piece 225, which protrudes through the skin of the residual limb 215. A torque absorber 230 may have been affixed to the connecting screw 220. The torque absorber 230 received a component connector 235 to which could be affixed a prosthetic 240.

Prior art devices such as those illustrated in FIGS. 1 and 2 often are not designed with consideration of the stresses that prostheses can induce on the residual limb. There remains a need for a prosthetic device for upper or lower limbs that reduces these stresses and, consequently, damage to the tissues of the residual limb.

SUMMARY OF THE INVENTION

Various illustrative embodiments of the present disclosure provide a prosthetic implant device and related methods. In accordance with one aspect of an illustrative embodiment of the present disclosure, the prosthetic device may include an internal component and an external component. The internal component may have an implant portion associated with one or more rare earth magnets. The internal component may be of a size and shape suitable for surgical implantation into the residual limb of the amputee. The implant portion may be of a size and shape suitable for surgical implantation into a bone within the residual limb of the amputee. The one or more rare earth magnets may generate at least one magnetic field. The external component may have a prosthetic connection. The prosthetic connection may include a cup and a piston. Each of the cup and piston is associated with its own plurality of magnetic elements. The magnet elements of the cup and the magnetic elements of the piston may each generate at least one magnetic field that may be in adaptable magnetic association with the at least one magnetic field generated by the one or more rare earth magnets implanted into the residual limb.

In accordance with an alternative illustrative embodiment of the present disclosure, various methods are provided. An illustrative method may include implanting an internal component of a prosthetic implant device into a residual limb of an amputee. The internal component may have an implant portion associated with one or more rare earth magnets. The internal component may be of a size and shape suitable for surgical implantation into the residual limb of the amputee. The implant portion may be of a size and shape suitable for surgical implantation into a bone within the residual limb of the amputee. The one or more rare earth magnets may generate at least one magnetic field. The method may include disposing an external component of the prosthetic implant device in magnetic association with the internal component. The external component may include a cup and a piston. The cup may have a prosthetic connection associated with a plurality of magnetic elements. The piston may also be associated with its own plurality of magnetic elements. The magnetic elements of the cup and the magnetic elements of the piston may each generate at least one magnetic field that may be in adaptable magnetic association with the at least one magnetic field generated by the one or more rare earth magnets implanted into the residual limb.

BRIEF DESCRIPTION OF THE DRAWINGS

The following description, given by way of example and not intended to limit the invention to the disclosed details, is made in conjunction with the accompanying drawings, in which like references denote like or similar elements and parts, and in which:

FIGS. 11A to 11C are views of embodiments of magnets of a prosthetic implant device of the present disclosure;

FIGS. 13A to 13B are x-ray views of an embodiment of an internal component and an external component of a prosthetic implant device of the present disclosure surgically implanted into sheep when the prosthetic implant device is in a loaded condition;

DETAILED DESCRIPTION

Detailed embodiments of the present prosthetic implant device, system, and methods are disclosed herein; however, it is to be understood that the disclosed embodiments are merely illustrative of the prosthetic implant device, system, and methods that may be embodied in various forms. In addition, each of the examples given in connection with the various embodiments of the systems and methods are intended to be illustrative, and not restrictive. Further, the drawings and photographs are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present prosthetic implant device, system, and methods.

Figure 1:
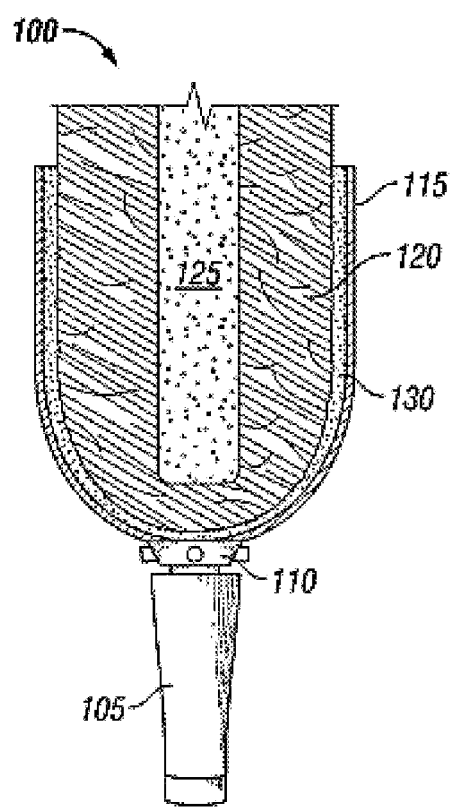
FIG. 1 is an illustrative embodiment of a prior art prosthetic device.
Figure 2:
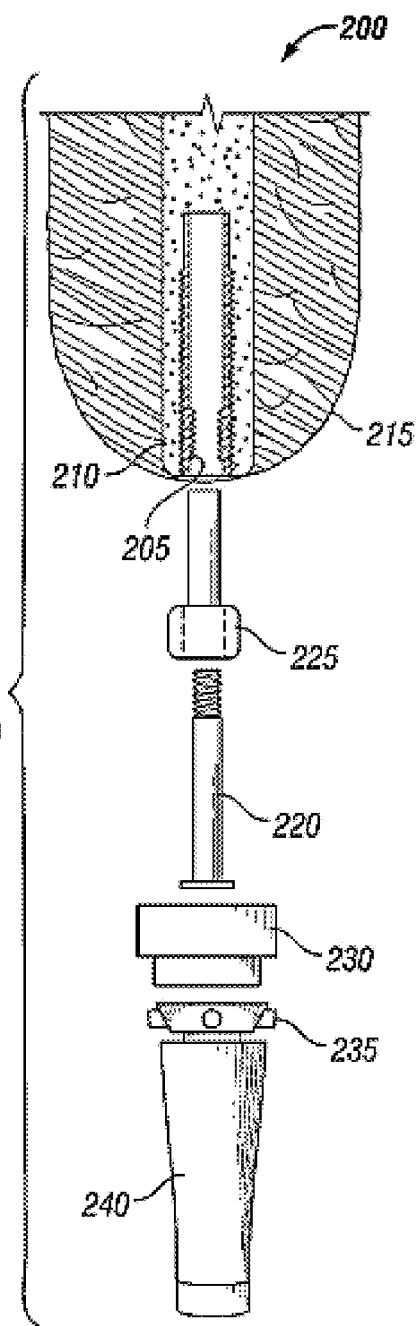
FIG. 2 is an exploded view of an illustrative embodiment of an alternative prior art prosthetic device.
Figure 3:
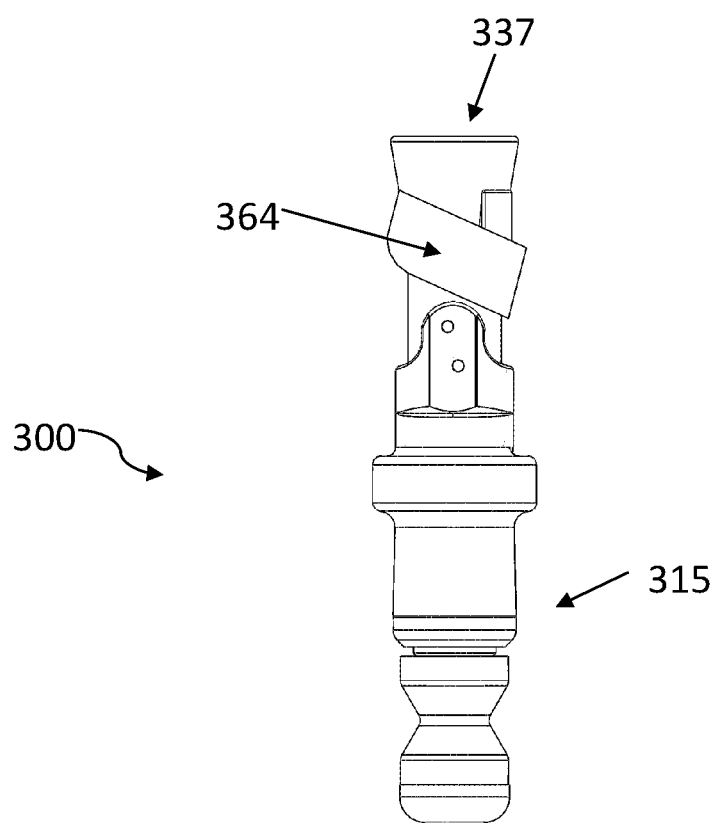
FIG. 3 is a perspective view of an amputated limb having a prosthetic implant device of the present disclosure.

With reference to FIG. 3, an embodiment of a prosthetic implant device 300 of the present disclosure is illustrated. The prosthetic implant device 300 is illustrated as engaged with an amputated leg (otherwise referred to herein as a residual limb 337). The prosthetic implant device 300 may include an internal component 310 (not shown) and an external component 315. The illustrative embodiment of FIG. 3 is non-limiting and prosthetic implant devices within the scope of this disclosure may be modified such that the prosthetic implant devices may be used with any amputated limb including, for example, a leg or arm of any animal including, without limitation, goats, cows, bulls, horses, dogs, cats, sheep, and primates including humans.

According to an embodiment, the external component 315 may include additional features and/or modifications to enhance its engagement, or association, with the residual limb 337. For example, as illustrated in FIG. 3, straps, buckles, and the like 364 may be used to facilitate the association with, or to further secure and/or align, the external component 315 to the amputated limb 337.

Figure 4:
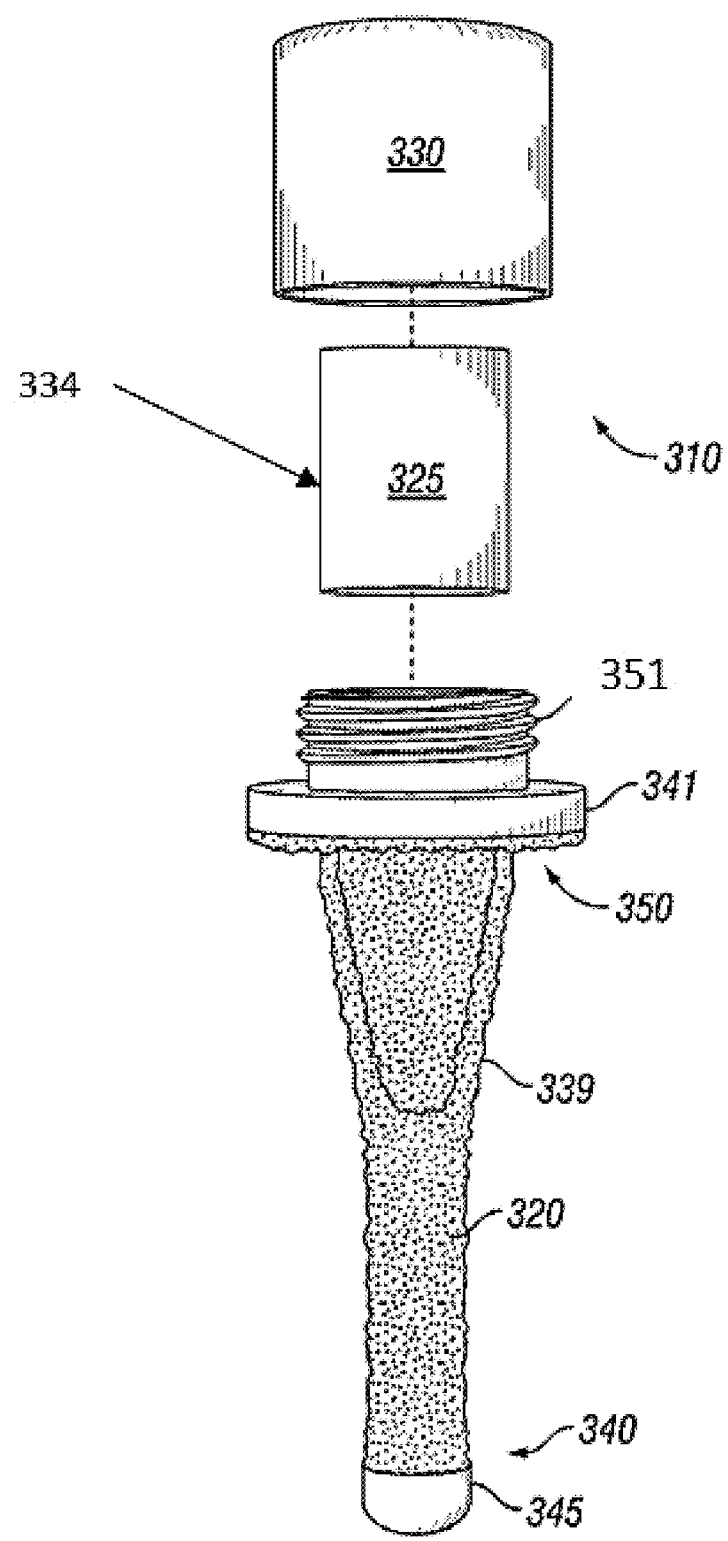
FIG. 4 is an exploded view of an embodiment of an internal component of a prosthetic implant device of the present disclosure.

FIG. 4 illustrates an embodiment of the internal component 310 of the prosthetic implant device 300. The internal component 310 may include at least an implant portion 320, one or more magnets 325, and an optional magnet housing 330. In an embodiment, the implant portion 320 may be of a size and shape suitable to be surgically fixed to, about, or within a patient's bone or skeleton of a residual limb. In an embodiment, the implant portion 320 may be of a size and shape suitable to form a friction fit within a surgically prepared hole, or cavity, within residual bone of an amputee's (or patient's) residual limb. In further embodiments, the implant portion 320 may include grooves (not shown) or biting ridges (not shown), which may be "screwed into" or otherwise engaged with a surgically prepared hole, or cavity within the residual bone of an amputee's (or patient's) residual limb.

In further embodiments, the implant portion 320 may include additional features and/or modifications to enhance its fit within the residual limb. For example, a first end 340 of the implant portion 320 may be capped with a metal, plastic, or ceramic cap 345 and a second end 350 of the implant portion 320 may blend, flare, or otherwise be integral with a shoulder 341. The shoulder 341—as with the entirety of the disclosed prosthetic implant device 300 and its component elements—may be of any size and shape depending on the particular limb and animal/person it is being designed to engage. In the embodiment with respect to FIG. 4, the shoulder 341 may be of a general cylindrical disk shape. A portion of the second end 350 extending past shoulder 341 of the implant portion 320 may further include connections such as threads 351, snaps, tabs, and the like suitable for receiving, engaging, and otherwise connecting the housing 330, which houses the one or more magnets 325, with the implant portion 320. Additionally, or alternatively, a portion of the shoulder 341 may include connections such as threads, snaps, tabs, and the like (not shown) suitable for receiving, engaging, and otherwise connecting the housing 330. In this embodiment, the housing 330 may include connections (not shown) for reciprocating engagement or connection with the implant portion 320. In an embodiment, within the housing 330 may be an array of one or more magnets 325.

In still further embodiments, the implant portion 320 may be manufactured from a variety of suitable materials, including those having the requisite strength and biocompatibility characteristics to function as the implant portion 320, including but not limited to any of the following, individually or in combination: graphite, pyrocarbon, ceramic, aluminum oxide, silicone nitride, silicone carbide or zirconium oxide; metal and metal alloys, e.g., Co—Cr—W—Ni, Co—Cr—Mo, CoCr alloys, CoCr molybdenum alloys, Cr—Ni—Mn alloys; powder metal alloys, 316L or other stainless steels, Ti and Ti alloys including Ti 6A1-4V ELI; polymers, e.g., polyurethane, polyethylene, polypropylene, thermoplastic elastomers, polyaryletherketones such as polyetheretherketone (PEEK) or polyetherketoneketone (PEKK); biomaterials such as polycaprolactone; and diffusion hardened materials such as Ti-13-13, zirconium and niobium. Moreover, the implant portion 320 may be coated with a coating 339 of a variety of suitable materials, including any of the following, individually or in combination, porous coating systems on bone-contacting surfaces, hydrophilic coatings on load-bearing surfaces, hydroxyapatite coatings on bone-contacting surfaces, and tri-calcium phosphate on bone-contacting surfaces. Suitable coatings may also include one or more growth factors and/or other biological agents such as bone morphogenetic proteins (BMP's), transforming growth factor beta, among others. In an embodiment, the coating 339 of the implant portion 320 may be harder than the implant portion 320 underneath the coating. Additionally, components of the invention may be molded or cast, hand-fabricated or machined.

The one or more magnets 325 may be formed of any magnetic material, and are preferably formed, contain, or are derived from rare earth metals, including without limitation scandium, yttrium, lanthanum, cerium, praseodymium, neodymium, promethium, samarium, samarium-cobalt, europium, gadolinium, terbium, dysprosium, holmium, erbium, thulium, ytterbium, lutetium, and combinations thereof, such as, for example, and without limitation, neodymiumiron-boron (Nd—Fe—B), samarium cobalt (Sm—Co), samarium iron nitride (Sm—Fe—N), cerium-cobalt permanent magnets (Ce(CuCo)$_5$), as well as other permanent magnets or magnetic materials including, without limitation, alnico alloys (Al—Ni—Co V), platinum-cobalt alloys (Pt—Co), iron based alloys, such as, iron-cobalt (FeCo), iron-platinum (FePt), hard ferrites, such as, Barium ferrite (BaFe.sub.$_{12}$O$_{19}$) or Strontium ferrite (SrFe$_{12}$O$_{19}$), magnetic shape memory alloys, such as, (Ni—Mn—Ga), manganese-bismuth permanent magnets (MnBi), and Cobalt-nickel-chromium alloys (Co—Ni—Cr). The housing 330 (shown in FIG. 4) may be formed of any material include plastics such as polyether-ether-ketone ("PEEK"), ceramics, and metals.

In an embodiment, the housing 330 may function as a physical barrier between the one or more magnets 325 and the limb or bone of the amputee so as to prevent physical contact with the magnets 325, which may not be biocompatible, while at the same time presenting a minimum amount of interference with the magnetic field generated by the one or more magnets 325. In an embodiment, the entirety of the implant portion 320 may be implanted within the residual limb of a patient or amputee. In this manner, the implant portion 320, the one or more magnets 325, as well as the housing 330, may be completely disposed inside of the residual limb and not visible without the aid of an x-ray machine or the like. Applied to the one or more magnets 325 may be one or more coatings or surface treatments 334, which Applicant presently believes may increase the biocompatibility of the one or more magnets 325 with the residual limb. Further to the above discussion, suitable coatings or surface treatments 334, which may be applied by any of a variety of applications such as spraying, painting, and the like to any of a variety of thicknesses generally ranging from about 100 nanometers to about 1 millimeter, may include, without limitation, nickel plating (nickel-copper-nickel), gold, titanium, titanium nitride, chromium nitride, palladium, stainless steel, polytetrafluoroethylene (often sold under the DuPont trademark Teflon™), and the like. Thus, the internal component 310 may be entirely sub-dermal, and Applicant presently believes the internal component 310 may be inserted in a single surgery; optionally, during the original amputation surgery. Without wishing to be bound by the theory, Applicant presently believes that the risk to outside infection may be eliminated (or otherwise reduced) because there are no transcutaneous elements to attract contaminants.

Figure 5:
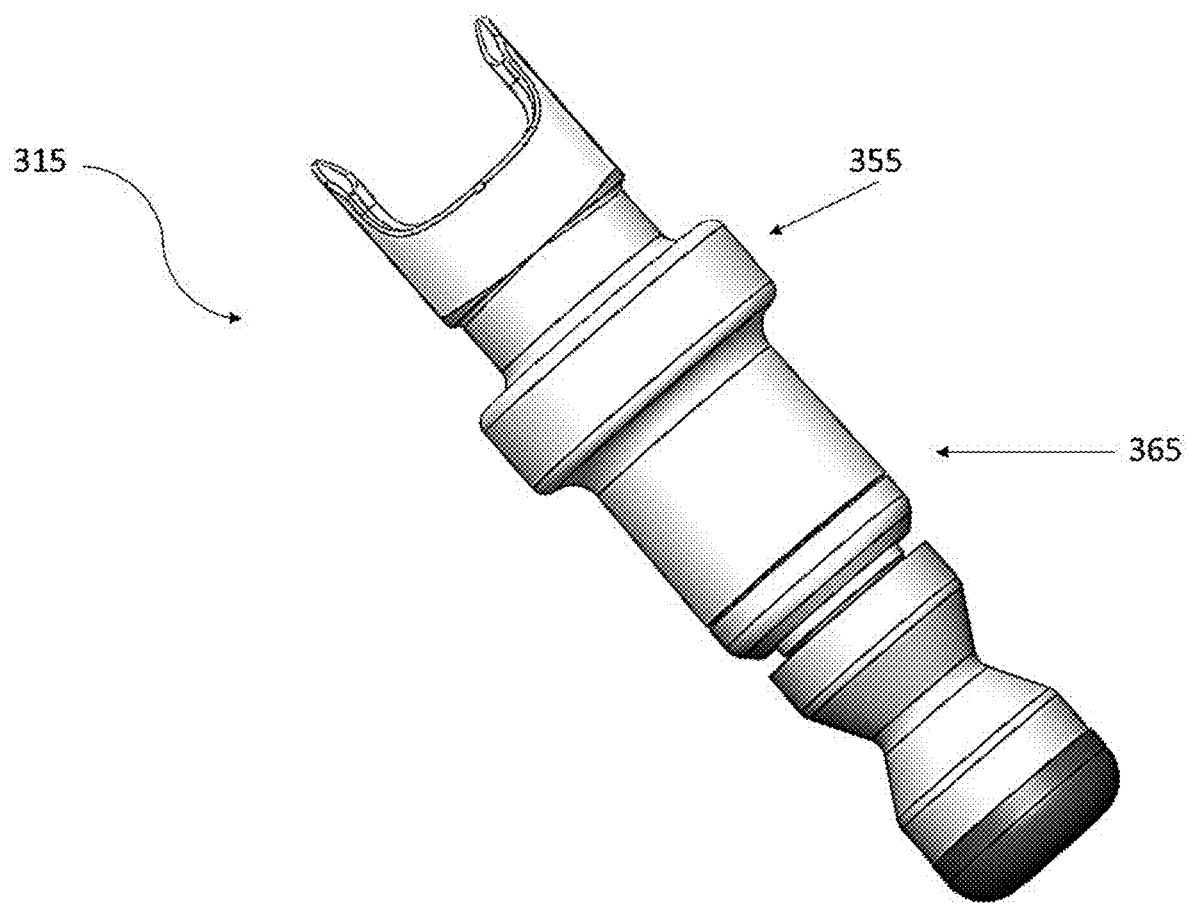
FIG. 5 is a perspective view of an embodiment of an external component of a prosthetic implant device of the present disclosure.
Figure 6B:
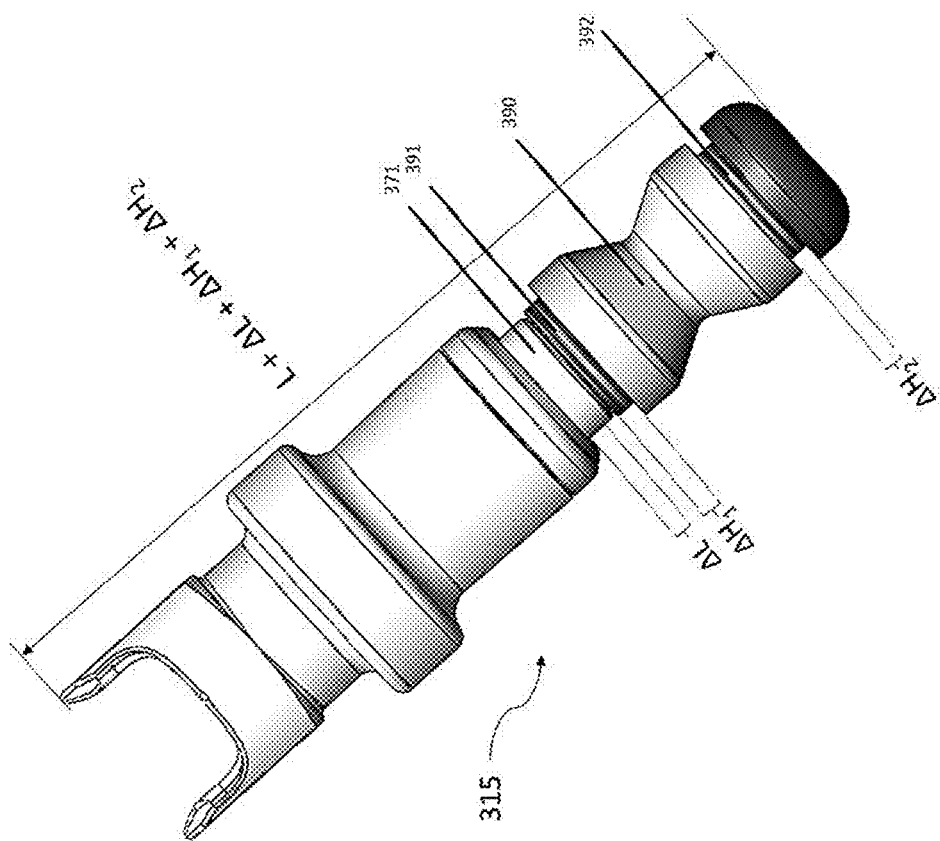
FIG. 6B is a perspective view of an embodiment of an external component of a prosthetic implant device of the present disclosure in an extended, unloaded condition.
Figure 6A:
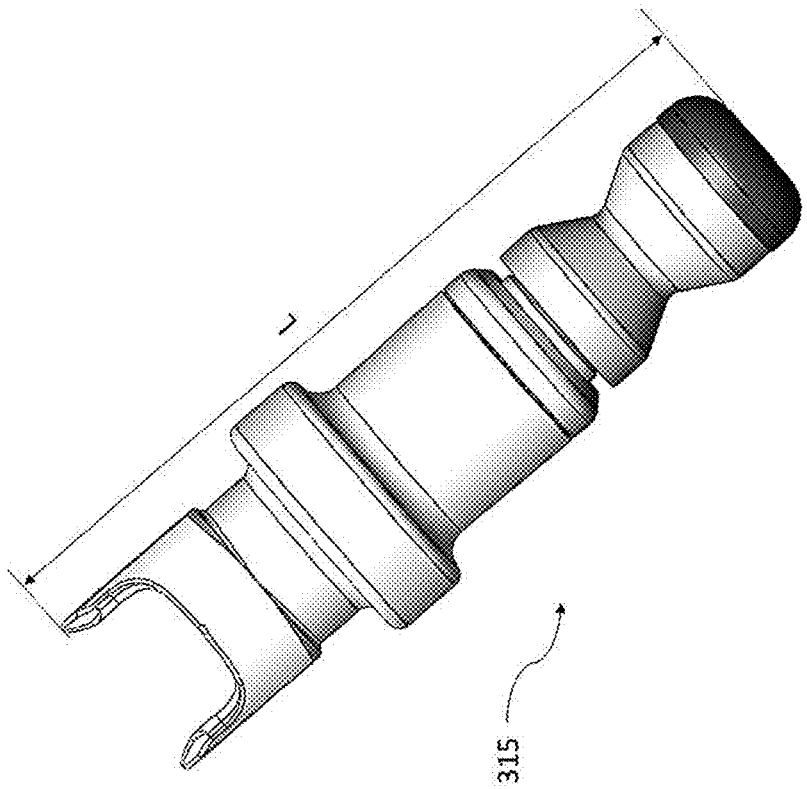
FIG. 6A is a perspective view of an embodiment of an external component of a prosthetic implant device of the present disclosure in an non-extended, loaded condition.

FIGS. 5 and 6 illustrate an embodiment of an assembled version of the external component 315 of the prosthetic implant device 300. The external component 315 is made up of a prosthetic cup 355 and a prosthetic piston 365. The prosthetic cup 355 has a socket 357 that includes a "sleeve" or "jacket" 336 (illustrated by FIGS. 7, 9B) that is placed over the residual limb 337 and may house external magnets in an array configuration, which is discussed in detail below. The prosthetic piston 365 threads onto a lower portion of the prosthetic cup 355, thereby creating an assembled external component 315. As illustrated by FIGS. 6A and 6B, the length "L" of the external component 315 is affected by displacement of a linear motion shaft 371 ($\Delta L$) and adjustable height of adaptors 391 ($\Delta H_1$) and 392 ($\Delta H_2$). The displacement of the linear motion shaft 371 ($\Delta L$) is dependent upon the phase of the gait cycle. The adjustable pylon 390 is adjusted via two independent adaptors 391 and 392, which are attached to each end of the adjustable pylon 390. The height of adaptor 391 $\Delta H_1$ and the height of adaptor 392 ($\Delta H_2$) are modified to ensure stance and gait are not altered after amputation. According to embodiments, $\Delta H_1$ and $\Delta H_2$ are the same. According to other embodiments, $\Delta H_1$ and $\Delta H_2$ are different. As discussed in further detail below, in its non-extended state (illustrated by FIG. 6A), external component 315 has a length of "L", while in an extended state (illustrated by FIG. 6B), external component 315 has a length of "L+$\Delta L$+$\Delta H_1$+$\Delta H_2$". The overall change in the length ensures that a user's gait cycle and stance can be adequately maintained after limb amputation. According to embodiments of the invention, the unextended length "L" of external component 315 may range from about 5 to about 24 inches, while the extended length "L+$\Delta L$+$\Delta H_1$+$\Delta H_2$" maybe range from about 5 to about 26 inches. According to at least one embodiment, the length of the external component 315 without including the adjustable pylon 390 and the two adaptors 391 and 392 is from about 3 to about 9 inches.

Figure 7:
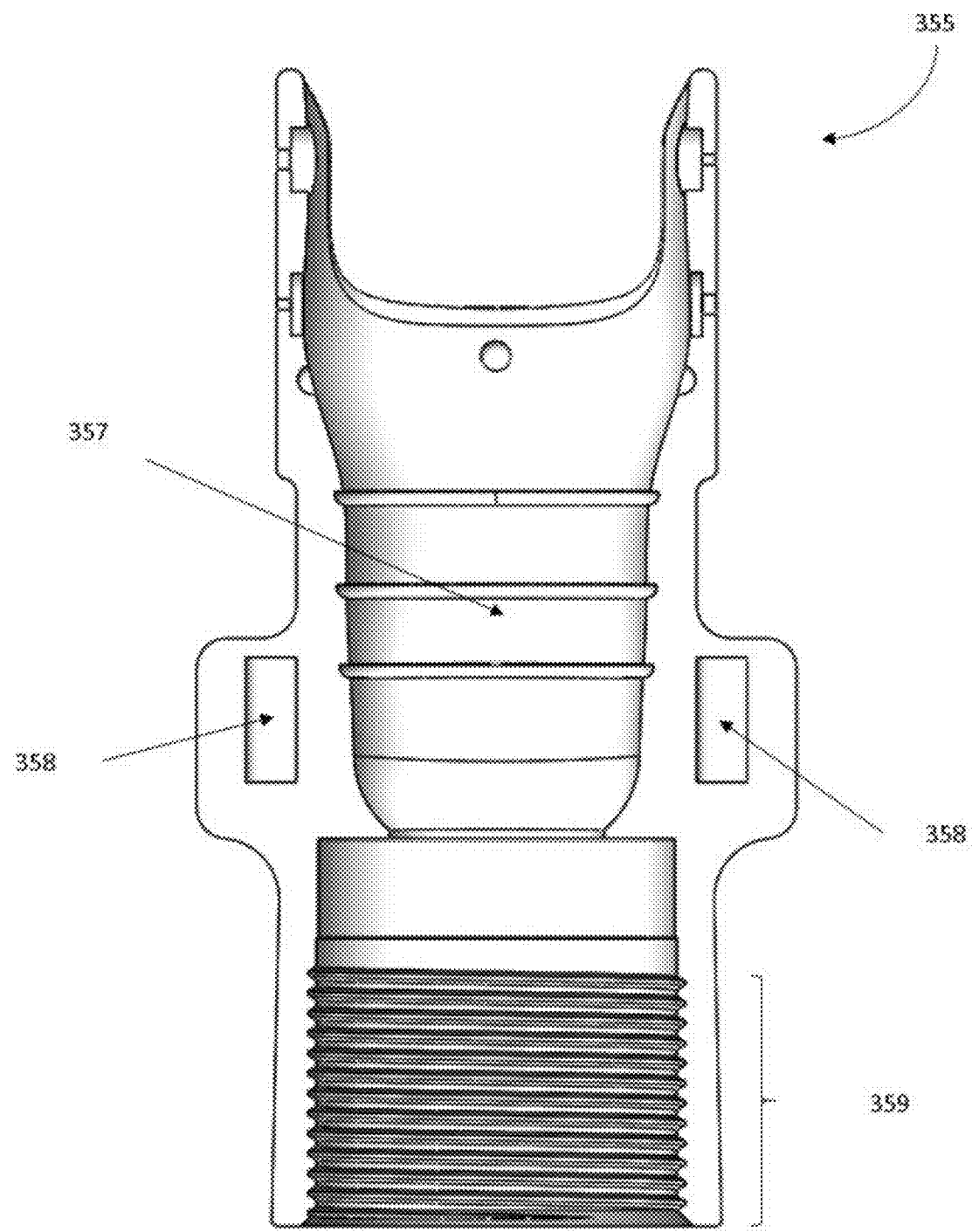
FIG. 7 is a front cut-away view of an embodiment of a prosthetic cup of an external component of a prosthetic implant device of the present disclosure.

FIG. 7 illustrates a front cut-away view of prosthetic cup 355 according to an embodiment. The prosthetic cup 355 may be made out of materials such as nylon, polypropylene, acrylics and the like. Prosthetic cup 355 includes a socket 357 for housing the residual limb 337. Prior to insertion into socket 357 of the prosthetic cup 355, the residual limb 337 is fitted with a sleeve or gel liner 336 (illustrated by FIG. 9B) for comfort and/or fit. The internal surface dimensions of the prosthetic cup 355 are customizable to the general shape (height, circumference, and width) of the residual limb 337. In some embodiments, the internal surface of the prosthetic cup 355 is generally circular, having a diameter that ranges from about 0.75 to about 6 inches. Sections of the internal surface of the prosthetic cup 355 may be oval-shaped in order to fit the geometry of the residual limb 337. The internal surface of socket 357 may contain features, such as ridges, indentations or protrusions (not shown), which may provide a method for mechanical interlocking with the outside of the gel liner/sleeve 336. Prosthetic cup 355 further includes internal threading 359, which is used to attach prosthetic cup 355 to prosthetic piston 365 (illustrated by FIGS. 9A to 10B). As discussed in further detail below, prosthetic cup 355 houses magnet array 358, which may be used to assist with residual limb stabilization.

Figure 8:
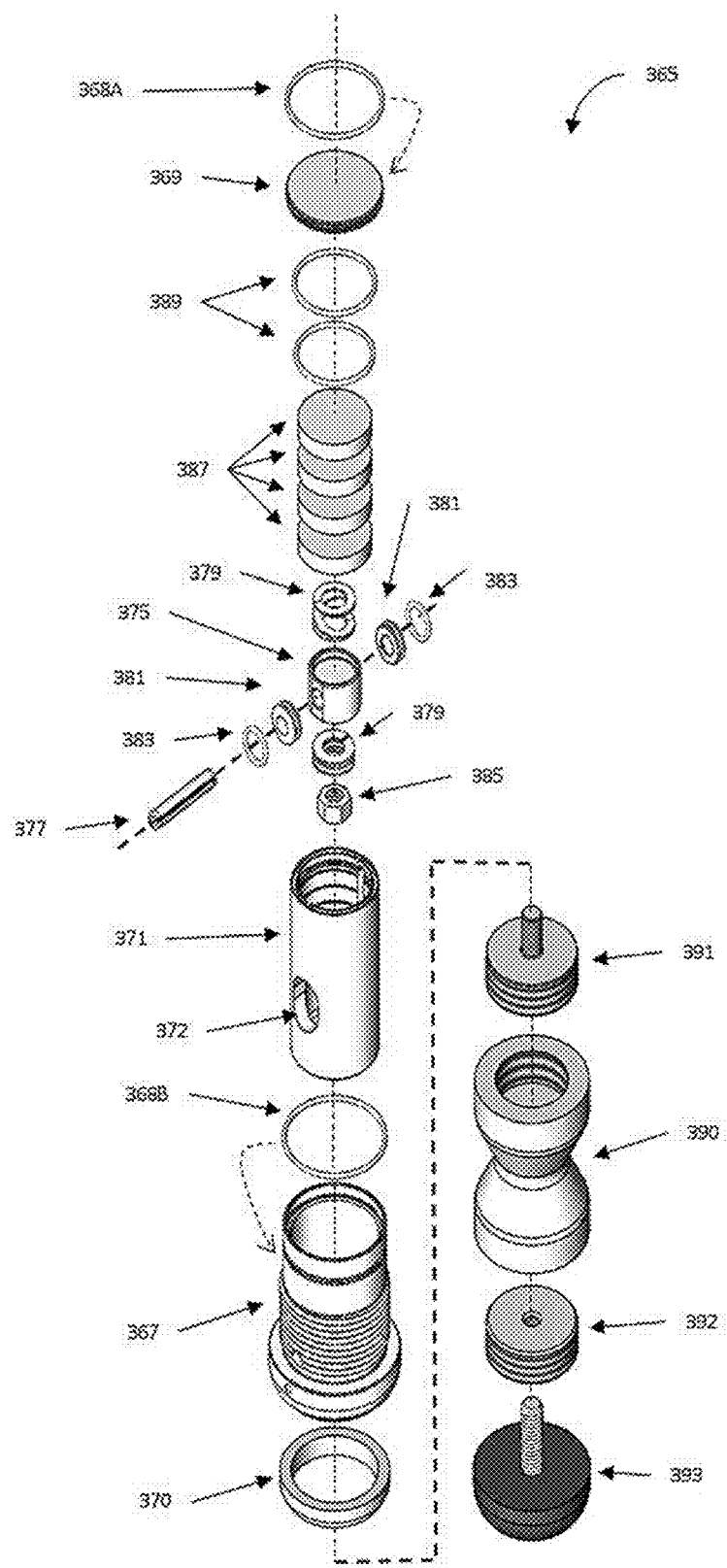
FIG. 8 is an exploded view of an embodiment of a prosthetic piston of an external component of a prosthetic implant device of the present disclosure.

FIG. 8 illustrates an exploded view of a prosthetic piston, according to an embodiment. The prosthetic piston 365 includes a bearing cylinder 367, which has threading on its exterior that is complementary to internal threading 359 of prosthetic cup 355. The prosthetic piston 365 can be attached to the prosthetic cup 355 by fastening or screwing internal threading 359 onto the threading of bearing cylinder 367 (as illustrated by FIGS. 9A to 10B). Linear motion shaft 371 is contained within the bearing cylinder 367 and houses one or more magnets 387 (also referred to as linear motion shaft magnets). Additionally, O-rings 389 are press-fit onto the one or more magnets 387 in order to ensure that they are adequately fixed within linear motion shaft 371. As discussed in further detail below, according to an embodiment, each magnet 387 is a rare earth magnet that is oriented such that the magnetic poles of each magnet 387 are axial and in opposition to the magnetic poles of the one or more implanted magnets 325 of the internal component 310, such that a repulsive force is generated between the one or more implanted magnets 325 and the one or more magnets 387. The number of magnets 387 housed in the linear motion shaft may be varied based on the desired strength of the repulsion force, i.e., more magnets means a larger repulsion force is generated. Each magnet, according to embodiments, has a height of between about 0.25 and about 1 inch, with an overall diameter of between about 0.5 and about 4 inches. Without wishing to be bound by the theory, the repulsive force between the implanted one or more magnets 325 and the one or more magnets 387 of prosthetic piston 365 reduce the compressive forces experienced by the soft tissues 338 of the residual limb 337 and transfer a portion of the weight bearing force to the bone 335. In other words, the adaptable magnetic association between the implanted one or more magnets 325 and the one or more magnets 387 of prosthetic piston 365 reduce the compressive forces experienced by the soft tissues 338.

Movement of linear motion shaft 371 is restricted within the bearing cylinder 367 via shuttle pin 377. According to an embodiment, the range of motion of the linear motion shaft 371 is controlled via interactions between shuttle body 375, shuttle edges 381, as well as oval shaped track 372 formed in linear motion shaft 371. As discussed in further detail below, shuttle pin 377 is placed through holes located on the sides of shuttle body 375, the oval shaped track 372, and holes located in bearing cylinder 367. In this way, shuttle body 375 and shuttle edges 381 remain in a fixed location within bearing cylinder 367. Shuttle edge 381 and O-ring 383 are located on each portion of shuttle pin 377 that extends between shuttle body 375 and bearing cylinder 367.

Figures 9A, 9B:
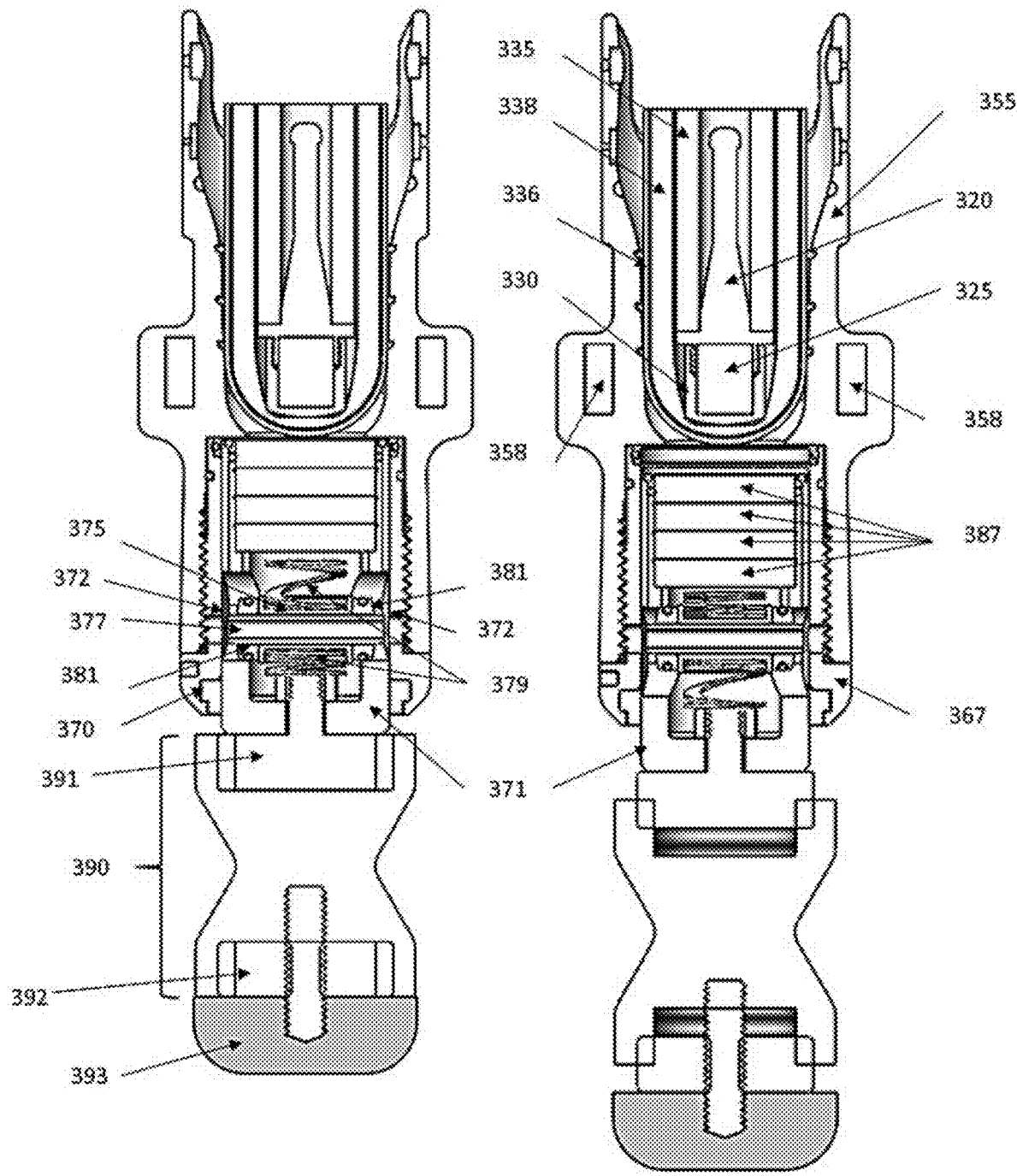
FIG. 9A is a front cut-away view of an embodiment of a prosthetic implant device of the present disclosure in an non-extended, loaded condition.
FIG. 9B is a front cut-away view of an embodiment of a prosthetic implant device of the present disclosure in an extended, unloaded condition.
Figure 10B:
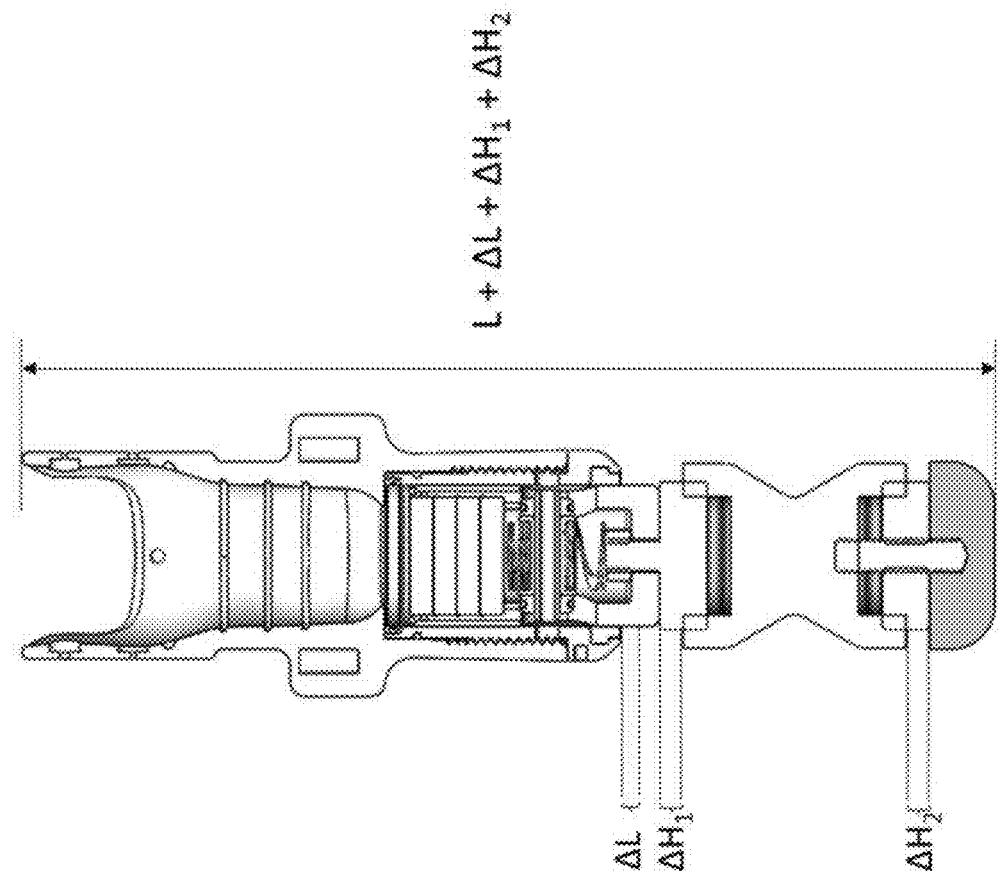
FIG. 10B is a front cut-away view of an embodiment of an external component of a prosthetic implant device of the present disclosure in an extended, unloaded condition.

When assembled, each shuttle edge 381 is located within the oval shaped track 372 of linear motion shaft 371. In this configuration vertical displacement of linear motion shaft 371 (i.e., $\Delta L$) is limited by contact of the top and bottom of oval shaped track 372 with shuttle edges 381. The height of oval shaped track 372 is selected based upon the amount of motion desired from the prosthetic implant device. According to embodiments, the height of oval shaped track 372 ranges from about 0.5 to about 1.5 inches. O-rings 383 are associated with each shuttle edge 381 and are configured to dampen the contact forces experienced as the linear motion shaft 371 cycles up and down. Springs 379 are located above and below shuttle body 375 in order to dampen the load on shuttle edges 381 that occurs during movement of the linear motion shaft 371. Springs 379 may also supply a force on linear motion shaft 371 in order to help to maintain the linear motion shaft 371 in its lowest position (e.g., as illustrated by FIGS. 9B and 10B) in an unloaded state. According to embodiments, the restricted movement of linear motion shaft allows for the distance between one or more magnets 387 and one or more implanted magnets 325 to range from about 5 mm to about 12 mm, which takes into account limitations from the prosthetic piston 365, soft tissue from limb 337 and the gel liner 336. In this way, the one or more magnets 387 and one or more implanted magnets 325 are in adaptable magnetic association with each other.

In order to seal components located within bearing cylinder 367, cap 369 is placed on the top of bearing cylinder 367. O-rings 368A and 368B are provided on both sides of cap 369 in order to create a press-fit between the cap 369 and the bearing cylinder 367. O-ring 368A is configured to be placed on a groove located around the perimeter of cap 369 while O-ring 368B is configured to be placed on a groove located on the outside of bearing cylinder 367. Additionally, wiper seal 370 is press-fit onto the bottom of the bearing cylinder 367 and is in contact with linear motion shaft 371 in order to prevent debris from entering the prosthetic piston.

As further illustrated by FIGS. 8-10B, attached to the bottom of linear motion shaft 371 is a first adaptor 391. First adaptor 391 includes a central, threaded shaft that is placed within a hole located in the bottom of linear motion shaft 371. In order to attach first adaptor 391 to linear motion shaft 371, nut 385 is threaded onto the central, threaded shaft once the shaft is placed through the hole in linear motion shaft 371. Additionally, the bottom, body portion of first adaptor 391 is threaded so that adjustable pylon 390 can be screwed thereon. Adjustable pylon 390 includes two threaded holes. The top threaded hole is configured to engage and screw onto first adaptor 391, while a bottom threaded hole is configured to engage and screw onto the threaded body of second adaptor 392. According to an embodiment, and as illustrated by FIGS. 8-10B, adjustable pylon 390 is hourglass shaped. However, adjustable pylon 390 is not so limited and other shapes are within the scope of the invention. For example, adjustable pylon 390 may be cylindrically or spherically shaped so long as the top and bottom threaded holes can be securely fastened to the two adaptors. Second adaptor 392 includes a threaded hole that is configured to engage with a central threaded shaft of bumper 393. Bumper 393, according to an embodiment, is a hemispherically shaped rubber bumper. However, bumper 393 is not so limited and other shapes are within the scope of the invention. Additionally, instead of bumper 393 other elements may be attached to second adapter 392. For example, a prosthetic foot, hand, paw, hoof, etc. may be used instead of bumper 393. In this way, external component 315 can be adapted for use with any type of residual limb for any type of animal.

Figure 10A:
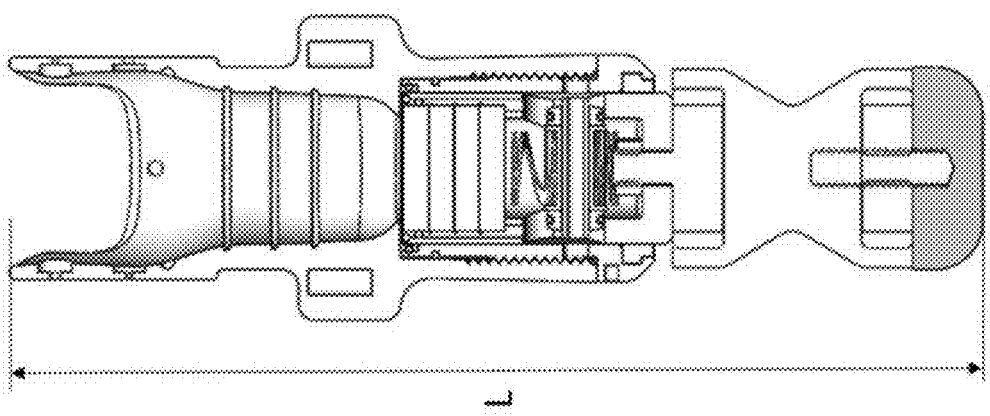
FIG. 10A is a front cut-away view of an embodiment of an external component of a prosthetic implant device of the present disclosure in an non-extended, loaded condition.

As discussed above, first adaptor 391 and second adaptor 392 screw into the top and bottom holes of adjustable pylon 390. The amount each adaptor is screwed into adjustable pylon 390, which allows the first adaptor 391 and second adaptor 392 to have adjustable heights (i.e., $\Delta H_1$ and $\Delta H_2$, respectively) and the overall length of external component 315 to be changed. For example, the overall length "L" of external component 315 may have no extensions (i.e., $\Delta H_1$ and $\Delta H_2=0$) when first adaptor 391 and second adaptor 392 are completely screwed into adjustable pylon 390, as illustrated by FIGS. 6A 9A, and 10A. Conversely, when first adaptor 391 and second adaptor 392 are only partially screwed into adjustable pylon 390, the overall length "L" of external component 315 is extended by the amount each of first adaptor 391 and second adaptor 392 extend from the top and bottom of adjustable pylon 390 (i.e., $\Delta H_1+\Delta H_2$), as illustrated in FIGS. 6B, 9B, and 10B. In this way, each adaptor is adjusted as needed to ensure that the overall height of the prosthetic device is appropriate for the specific limb the device is attached to (e.g., in embodiments in which the prosthetic device is used on a lower limb, the overall height is appropriate to preserve the individual's gait). According to embodiments, each adaptor may have a height within the range of between about 0.25 and about 2 inches. However, the invention is not so limited and the height of each adaptor may vary according to each individual user's needs. The overall height of adjustable pylon 390 may also vary according to each individual user's needs.

According to embodiments where the prosthetic device is attached to a lower limb, at mid stance of a gait cycle, bumper 393 is in contact with the ground forcing linear motion shaft 371 to move to the highest position in relation to the prosthetic socket. At this highest position, as illustrated by FIGS. 6A, 9A and 10A, the repulsive magnetic force is strongest (magnet(s) 387 are closest to magnet(s) 325 in the residual limb 337). At this position, the shuttle edges 381 are in contact with the bottom of the oval-shaped track 372 in linear motion shaft 371. The repulsive magnetic force will transfer some of the ground reaction force to the implant/bone of the residual limb 337 and thus protect soft tissue of the residual limb 337 from experiencing high contact pressures from the socket 357 of the prosthetic cup 355. During the swing portion of the gait cycle, the bumper 393 is no longer in contact with the ground, allowing the linear motion shaft to move to the lowest position (e.g., $\Delta L$ of external component 315 is at a maximum). At this lowest position, as illustrated by FIGS. 6B, 9B, and 10B, the magnetic force is weakest (magnet(s) 387 are furthest from the magnet(s) 325 in the residual limb 337) and the shuttle edges 381 are in contact with the top of the oval-shaped track 372 in linear motion shaft 371.

According to an aspect of the invention, the magnetic repulsion field created between the one or more implanted magnets 325 of the internal component 310 and the one or more magnets 387 located within linear motion shaft 371 exerts lateral forces on the internal component 310 and the external component 315. These lateral or side forces move the one or more implanted magnets 325 within the residual limb 337 off-center from the one or more magnets 387 located within linear motion shaft 371, reducing the axial repulsion forces between these magnets. The addition of magnet array 358 located within prosthetic cup 355 reduces or minimizes these lateral or side forces and helps to ensure that the one or more implanted magnets 325 and the one or more magnets 387 remain collinear or nearly collinear, ensuring that the axial repulsion force is optimally maintained. As discussed in further detail below, the reduction in the lateral forces is accomplished, according to at least one embodiment, using a plurality of cylindrical magnets that are configured to form a ring shape, the ring having a central axis that is coaxial with the one or more implanted magnets 325 and coaxial with the one or more magnets 387. According to another embodiment, the reduction in the lateral forces is accomplished using a single ring-shaped magnet, the ring having a central axis that is coaxial with the one or more implanted magnets 325 and coaxial with the one or more magnets 387.

Simulations were run with a vertical axial separation of 5 mm from the central axes of the one or more implanted magnets 325 and the one or more magnets 387, as illustrated by FIG. 11A. The 5 mm axial separation was chosen in order to mimic potential maximal lateral forces. The combination of the placement location, magnet size, number of magnets, and magnetic pole orientation of magnet array 358 was assessed through mathematical modeling of the resultant magnetic force fields using JMAG software (e.g., Powersys Inc, Southfield, Mich.).

FIGS. 11B, 11C, 12A, and 12B illustrate different configurations of magnet array 358 in relation to the one or more implanted magnets 325 and the one or more magnets 387 located within linear motion shaft 371, according to embodiments of the invention, based upon the mathematical modeling. According to one embodiment, each magnet in magnet array 358 has an axial magnetic orientation (i.e., a magnetic orientation that is parallel to the one or more implanted magnets 325 and the one or more magnets 387), as illustrated by FIG. 11B. According to another embodiment, each magnet in magnet array 358 has a diametric magnetic orientation (i.e., a magnetic orientation that is perpendicular to the one or more implanted magnets 325 and the one or more magnets 387), as illustrated by FIG. 11C. In each of these embodiments, magnet array 358 comprises six cylindrical magnets that are in a ring configuration. The cylindrical magnets are preferably located with the transverse center of the ring in line with the transverse center of the one or more implanted magnets 325 implanted in the residual limb before any lateral forces are experienced. In this configuration, the ring created by the cylindrical magnets also has a center that is co-axial with the one or more magnets 387 when the external component 365 is attached to the residual limb. However, additional or fewer magnets are within the scope of magnet array 358 of these embodiments. Using mathematical modeling it was found that having an axial magnetic orientation reduces the lateral forces by roughly 5%, while lateral forces were reduced by roughly 3% when magnet array 358 has a diametric magnetic orientation.

Figure 12A:
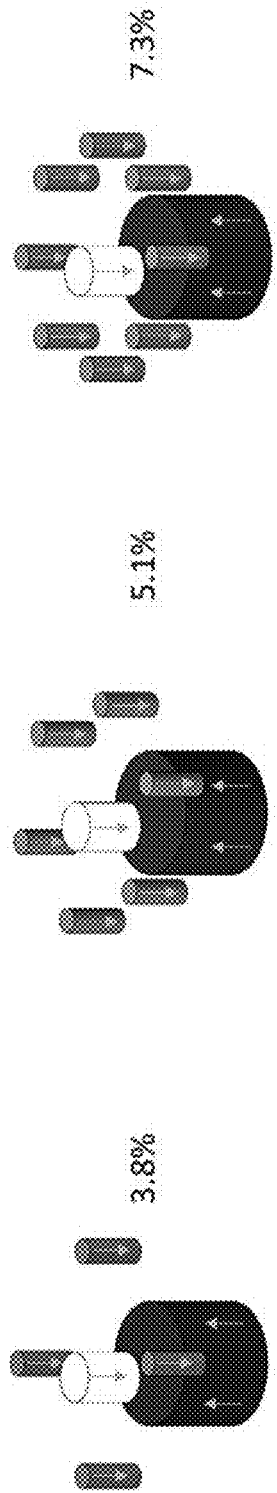
FIGS. 12A to 12B are views of additional embodiments of magnets of a prosthetic implant device of the present disclosure.
Figure 12B:
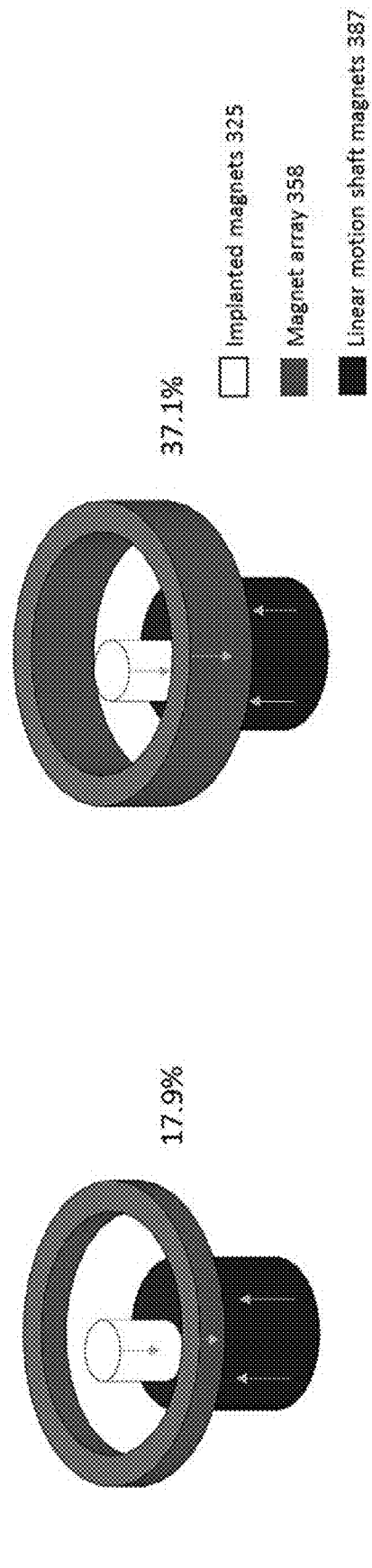

According to other embodiments, differing numbers of cylindrical, axial magnetic oriented, magnets are used in magnet array 358. According to one embodiment, magnet array 358 comprises four magnets, as illustrated by FIG. 12A. Alternatively, magnet array 358 comprises eight magnets, as further illustrated by FIG. 12A. Using mathematical modeling it was found that having eight magnets reduces the lateral forces by roughly 7%, while lateral forces were reduced by roughly 3% when magnet array 358 has four magnets. These reductions are based on the magnets of magnet array 358 having an axial magnetic orientation. Although embodiments are described using four, six, and eight magnets, the invention is not so limited and other amounts of magnets having different shapes are within the scope of the invention. For example, magnet array 358 may comprise three, five, seven, or nine magnets so long as the magnets are arranged in a shape that exerts magnetic forces equally around the one or more implanted magnets 325. The magnets may also not be cylindrical. Instead, the magnets of magnet array 358 may be disc shaped, spherical, rectangular, square, etc. According to another embodiment, magnet array 358 comprises a single, solid, ring-shaped magnet, as illustrated by FIG. 12B.

According to the above embodiments, the height of the ring-shaped magnet or cylindrical magnets in the array configuration are similar or equal to the height of the one or more magnets 325 implanted in the residual limb. Although, due to weight constraints, the height of the magnet(s) of magnet array 358 may be less than one half the height of the one or more implanted magnets 325, while still maintaining nearly half the reduction in lateral forces. Based upon anatomical, manufacturing, and size and weight considerations, according to a preferred embodiment, magnet array 358 comprises 6 to 8 magnets of a cylindrical geometry, with a height equal to and diameter of approximately one half that of the height and diameter of the one or more magnets 325 implanted into the residual limb, with the magnets of the magnet array 358 magnetized in the axial direction. According to this embodiment, the transverse center of the magnet array 358 is aligned with the transverse center of the one or more magnets 325 implanted within the residual limb. Other combinations of the system can be chosen based upon differing design considerations of the prosthetic construct desired.

EXAMPLES/EXPERIMENTS

A sheep was used in the experiment as described hereinafter. Surgical and animal care procedures were performed in accordance with federal requirements (Animal Welfare Act) following IACUC review/approval.

The sheep underwent unilateral amputation of the forelimb at the mid-metacarpal. A titanium alloy implant, with commercially pure titanium spray coating and hydroxyapatite coating was inserted into the medullary canal of each animal's amputated forelimb. A PEEK housing was threaded to a distal implant end, and hermetically sealed a nickel-plated (Ni—Cu—Ni), gold-coated neodymium (NdFeB) N52-grade magnet (1.27 cm diameter, 1.59 cm height) from tissue contact. Anatomical measurements and cast moldings of the residual limb were used to construct an external component.

The highest and lowest positions of the prosthetic piston mechanism are demonstrated in the radiographic images using the magnet implant placed in an amputated limb of a sheep, as illustrated in FIGS. 13A-14B. These images show the prosthetic cup 355 without magnet array 358. As seen in FIG. 13A, which is a sagittal view, the prosthetic cup is 355 slightly radiolucent, but remains visible. Within the socket 357 of the prosthetic cup 355 is the gel liner 336, soft tissues 338, bone 335, and internal component 310. The implanted magnet housing 330, which contains the implant magnet 325, is radiolucent; however, the threads that attach the magnet housing 330 onto implant portion 320 are clearly visible. The components visible in the prosthetic piston are the bearing cylinder 367, linear motion shaft 371, shuttle pin 377, shuttle edges 381, nut 385 and magnets 387. Other components such as the shuttle body 375, O-rings 383, and springs 379 are less visible due to the relative radiolucency of the materials. Oval-shaped track 372 cut into the linear motion shaft 371 is clearly visible, as seen in FIG. 13B, which is a coronal view.

Figure 14B:
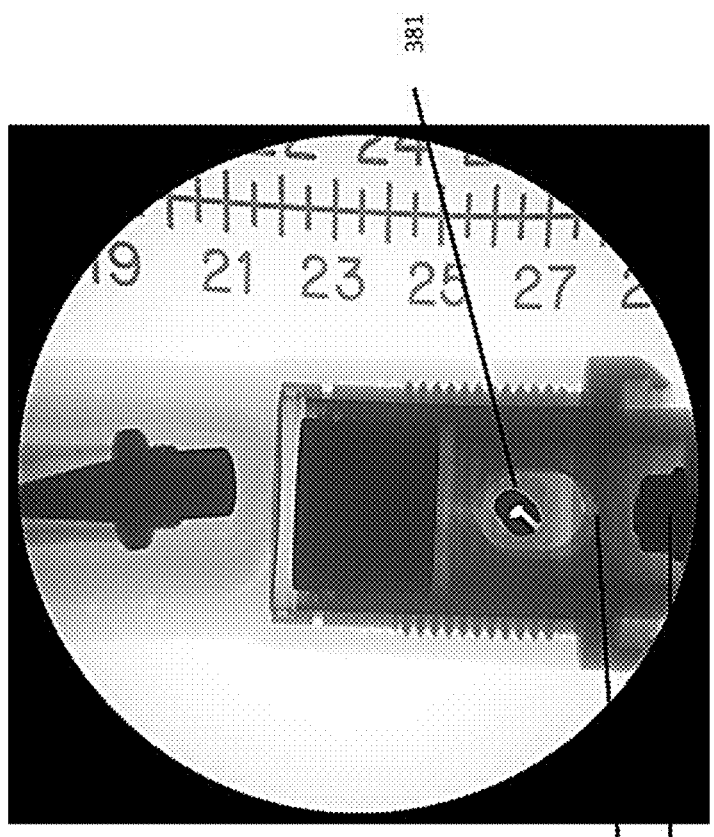
FIGS. 14A and 14B are x-ray views of an embodiment of an internal component and an external component of a prosthetic implant device of the present disclosure surgically implanted into sheep when the prosthetic implant device is in an unloaded condition.
Figure 14A:
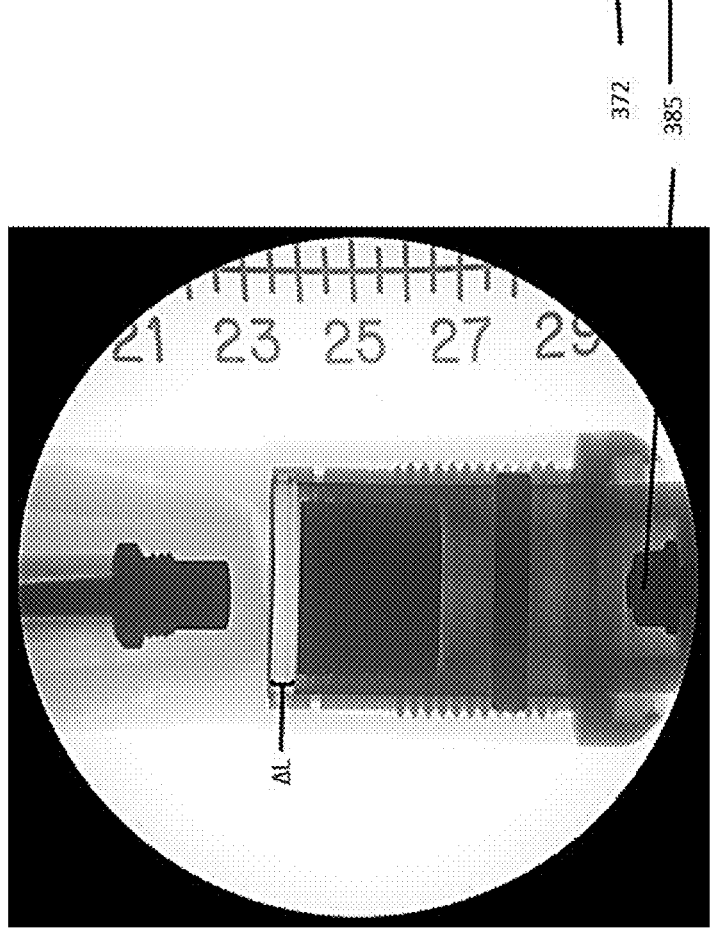

At the highest position, as illustrated by FIGS. 13A and 13B, magnets 387, which are housed within the linear motion shaft 371, are nearly coincident with the top of housing 330. This position occurs during mid stance of the gait cycle at which the distance between the implant magnet and prosthetic magnets is smallest and the repulsion force generated is strongest. In the coronal view of FIG. 13B, the shuttle edge 381 is in contact with the bottom of the oval-shaped track 372 in the linear motion shaft 371. At the lowest position, as illustrated by FIGS. 14A and 14B, the prosthetic magnets have moved a maximum distance away from the implanted magnets (ΔL). This position occurs during the swing portion of the gait cycle at which distance between implant magnet and prosthetic magnets is increased and the repulsion force generated is weakest. In the coronal view of FIG. 14B, the shuttle edge 381 is in contact with the top of the oval-shaped track 372 in the linear motion shaft 371.

Without wishing to be bound by the theory, in the present method and implants, the loads are transferred from a prosthesis to the skeleton, without the need for permanent skin penetrations. The implant may be embedded within the residual limb, and may react with the prosthetic socket to provide a stable, non-contact connection between the patient and the prosthesis.

We claim:

1. A prosthetic implant device comprising:
an internal component comprising:
   (a) an implant portion configured for implantation into a bone of a residual limb of an amputee; and
   (b) one or more first magnets associated with the implant portion; and
an external component comprising:
   (a) a prosthetic cup housing a magnet array that comprises one or more third magnets, the prosthetic cup configured to attach to the residual limb; and
   (b) a prosthetic piston configured to attach to the prosthetic cup, the prosthetic piston comprising:
      (i) a bearing cylinder configured to attach to the prosthetic cup; and
      (ii) a linear motion shaft located within the bearing cylinder, wherein the linear motion shaft houses one or more second magnets, the one or more second magnets being in adaptable magnetic association with the one or more first magnets; and
wherein the linear motion shaft is configured to linearly move relative to the bearing cylinder in response to loading.

2. The prosthetic implant device of claim 1;
wherein the one or more second magnets generate at least one magnetic field; and
wherein the magnetic array is configured to reduce lateral or side forces experienced by the one or more first magnets due to the at least one magnetic field generated by the one or more second magnets.

3. The prosthetic implant device of claim 1;
wherein the linear motion shaft comprises an oval-shaped track.

4. The prosthetic implant device of claim 3;
wherein the prosthetic piston further comprises:
   a shuttle body;
   a shuttle pin; and
   two shuttle edges;
wherein the shuttle body, the shuttle pin, and the two shuttle edges are at least partially located within the linear motion shaft and the bearing cylinder; and
wherein movement of the linear motion shaft within the bearing cylinder is restricted by the shuttle body, the shuttle pin, the two shuttle edges, the oval-shaped track, or a combination thereof.

5. The prosthetic implant device of claim 4;
wherein the shuttle body, the shuttle pin, and the two shuttle edges are in a fixed location relative to the bearing cylinder;
wherein the shuttle pin is at least partially located within the shuttle body; and
wherein one of the two shuttle edges is located at each end of the shuttle pin.

6. The prosthetic implant device of claim 4;
wherein movement of the linear motion shaft within the bearing cylinder is restricted by contact of at least one of the two shuttle edges with an end of the oval-shaped track.

7. The prosthetic implant device of claim 1;
wherein movement of the linear motion shaft within the bearing cylinder modifies the overall length of the external component.

8. The prosthetic implant device of claim 1;
wherein the prosthetic piston further comprises:
   a first adaptor;
   a second adaptor; and
   an adjustable pylon;
wherein each of the first adaptor, the second adaptor, and the adjustable pylon are configured to adjust the overall length of the external component.

9. The prosthetic implant device of claim 1;
wherein the implant portion is of a size and shape suitable for surgical implantation into a bone within a leg or arm of a dog, cat, cow, bull, horse, goat, sheep, non-human primate, or human.

10. The prosthetic implant device of claim 1;
wherein the internal component is configured to be entirely sub-dermal and the external component is designed to be entirely outside of the residual limb of the amputee.

11. The prosthetic implant device of claim 1;
wherein the one or more third magnets are in a ring configuration; and
wherein the magnet array is configured to surround the one or more first magnets.

12. The prosthetic implant device of claim 1;
wherein the one or more third magnets comprise a ring-shaped magnet; and
wherein the magnet array is configured to surround the one or more first magnets.

13. The prosthetic implant device of claim 1;
wherein the one or more third magnets comprise cylindrically shaped magnets.

14. The prosthetic implant device of claim 13;
wherein each of the one or more third magnets has a height that is equal to the height of the one or more first magnets.

15. The prosthetic implant device of claim 13;
wherein each of the one or more third magnets has a height that is less than the height of the one or more first magnets.

16. The prosthetic implant device of claim 1;
wherein the one or more third magnets have an axial magnetic orientation relative to the one or more first magnets.

17. The prosthetic implant device of claim 1;
wherein the one or more third magnets have a diametric magnetic orientation relative to the one or more first magnets.

* * * * *